(12) United States Patent
Korokhov et al.

(10) Patent No.: US 7,045,348 B2
(45) Date of Patent: May 16, 2006

(54) ADENOVIRAL VECTOR INCORPORATING ZIPPER PEPTIDE-MODIFIED FIBER PROTEIN AND USES THEREOF

(75) Inventors: Nikolay Korokhov, Birmingham, AL (US); Galina Mikheeva, Houston, TX (US)

(73) Assignee: Vectorlogics, Inc., Birmingham, AL (US)

( * ) Notice: Subject to any disclaimer, the term of this patent is extended or adjusted under 35 U.S.C. 154(b) by 313 days.

(21) Appl. No.: 10/624,218

(22) Filed: Jul. 22, 2003

(65) Prior Publication Data

US 2004/0171158 A1 Sep. 2, 2004

Related U.S. Application Data

(60) Provisional application No. 60/397,951, filed on Jul. 22, 2002, now abandoned.

(51) Int. Cl.
*C15N 15/861* (2006.01)
*C12N 15/64* (2006.01)
*A01K 63/00* (2006.01)

(52) U.S. Cl. .................. 435/320.1; 435/91.4; 435/455; 435/456; 424/93.2

(58) Field of Classification Search ...................... None
See application file for complete search history.

(56) References Cited

U.S. PATENT DOCUMENTS 6,210,946 B1  4/2001  Curiel et al.
6,284,742 B1  9/2001  Curiel et al.

OTHER PUBLICATIONS

Bodey et al., Failure of cancer vaccines: the significant limitations of this approach to immunotherapy, Anticancer Res. 20: 2665-2676, 2000.*
Radoja et al., "Cancer-induced defective cytotoxic T lymphocite effector function: another mechanism how antigenic tumors escape immune-mediated killing," Mol Med 6(6): 465-479, 2000.*
Basak et al., "Modifying adenoviral vectors for use as gene-based cancer vaccines," Viral Immunol. 17 (2): 2182-196, Jun. 2004.*

Arndt et al.; A Heterodimeric Coiled-coil Peptide Pair Selected in Vivo from a Designed Library-versus-Library Ensemble; J. Mol. Biol. (2000) 295, 627-639.
Asada-Mikami et al.; Efficient Gene Transduction by RGD-fiber Modified Recombinant Adenovirus into Dendritic Cells; Jpn. J. Cancer Res. 92, 321-327, Mar. 2001.
Banchereau & Steinman; Dendritic cells and the control of immunity: NATURE, vol. 392, Mar. 19, 1988: pp. 245-252.
Belousova et al., Generation of recombinant adenoviral vectors containing fiber proteins with extended HI-loops; Molecular Therapy vol. 3, No. 5, May 2001, S168.
Belousova et al., Genetically Targeted Adenovirus Vector Directed to CD40-Expressing Cells; Journal of Virology; Nov. 2003; vol. 77, No. 21; pp. 11367-11377.
Bewig & Schmidt; Accelerated Titering of Adenoviruses; Biotechniques, vol. 28, No. 5 (2000).
Bocchia et al., Antitumor vaccination: where we stand; Haematologica 2000; 85:1172-1206.
Boon et al., Tumor Antigens Recognized By T Lymphocytes. Thierry Boon, Jean-Charles Cerottini, Benoit Van den Eynde, Pierre van der Bruggen, Aline Van Pel: Annu. Rev. Immunol. 1994: 12-337-65.
Brand et al.; Liver-associated toxicity of the HSV-tk/GCV approach and adenoviral vectors: Cancer Gene Therapy, vol. 4, No. 1, 1997, pp. 9-16.
Brossart et al.; Virus-Mediated Delivery of Antigens Epilopes into Dendritic Cells as a Means to Induce CTL; The Journal of Immunology, 1997, 158:3270-3276.
Correale et al., In Vitro Generation of Human Cytotoxic T Lymphocytes Specific for Peptides Derived From Prostate-Specific Antigen; Journal of the National Cancer Institute; vol. 89, No. 4, Feb. 19, 1997.

(Continued)

*Primary Examiner*—Scott D. Priebe
(74) *Attorney, Agent, or Firm*—Frommer Lawrence & Haug LLP; Thomas J. Kowalski; Deborah L. Lu (57) ABSTRACT

The present invention provides a recombinant adenovirus vector targeted by zipper peptides. The vector contains a fiber protein modified by insertion of a first zipper peptide that can crosslink to a fusion protein comprising a second zipper peptide and a targeting ligand. Binding of the first zipper peptide to the second zipper peptide forms a targeted vector: ligand complex, thereby targeting the adenovirus vector to a cell that expresses a cell surface molecule that binds to said targeting ligand.

6 Claims, 5 Drawing Sheets

OTHER PUBLICATIONS

Coulie et al., Antigens recognized by T-lymphocytes on human tumours; Biochemical Society Transactions, vol. 25, 1997.

Dietz and Vuk-Pavlovic High Efficiency Adenovirus-Mediated Gene Transfer to Human Dendritic Cells: Blood. vol. 91. No. 2 (Jan. 15, 1998): pp. 392-398.

Dmitriev et al.; An Adenovirus Vector with Genetically Modified Fibers Demonstrates Expanded Tropism via Utilization of a Coxsackievirus and Adenovirus Receptor-Independent Cell Entry Mechanism: Journal of Virology, Dec. 1988, pp. 9706-9713.

Dmitriev et al.; Ectodomain of Coxsackievirus and Adenorvirus Receptor Genetically Fused to Epidermal Growth Factor Mediales Adenovirus Targeting to Epidermal Growth Factor Receptor-Positive Cells: Journal of Virology, Aug. 2000, pp. 6875-6884.

Douglas et al., A system for the propagation of adenoviral vectors with genetically modified receptor specificities: Nature Biotechnology, May 1999, vol. 17, pp. 470-474.

Fong and Engleman: Dendritic Cells in Cancer Immunotherapy: Annu. Rev. Immunol. 2000, 18:245-273.

Freimuth; A Human Cell Line Selected for Resistance to Adenovirus Infection Has Reduced Levels of the Virus Receptor; Journal of Virology. Jun. 1996, pp. 4081-4085.

Gong et al.; Reversal of tolerance to human MUCI antigen in MUCI antigen in MUCI transgenic mice immunized with fusions of dendritic and carcinoma cells; Proc. Natl. Acad. Sci. USA. vol. 95, pp. 6279-6283, May 1998.

Hodges; De novo design of α-helical proteins: basic research to medical applications: Biochem. Cell Biol. 74: 133-154 (1996).

Hong & Engler; Domains Required for Assembly of Adenovirus Type 2 Fiber Trimers; Journal of Virology, Oct. 1996, p. 7071-7078.

Hsu et al; Vaccination of patients with B-cell lymphoma using autologous antigen-pulsed dentrilic cells; Nature Medicine, vol. 2, No. 1, Jan. 1996, pp. 52-58.

Hurst; Transcription Factors I: bZIP proteins: Protein Profile, vol. 2, Issue 2, pp. 105-168.

Kaplan et al.; Induction of Antitumor Immunity with Dendritic Cells Transduced wtih Adenovirus Vector-Encoding Endogenous Tumor-Associated Antigens; The Journal of Immunology, Apr. 30, 1999, pp. 699-707.

Katz et al.; Green Fluorescent Protein Labeling of Cytoskeletal Structures—Novel Targeting Approach Based on Leucine Zippers; BioTechniques, vol. 25, No. 2 (1998), pp. 298-303.

Krasnykh et al.; Generation of Recombinant Adenovirus Vectors with Modified Fibers for Altering Viral Tropism: Journal of Virology, Oct. 1996, pp. 6839-6846.

Krasnykh et al.; Characterization of an Adenovirus Vector Containing a Heterologous Peptide Epitope in the HI Loop of the Fiber Knob; Journal of Virology, Mar. 1998, pp. 1844-1852.

Krasnykh et al.; Genetic Targeting of an Adenovirus Vector via Replacement of the Fiber Protein with the Phage T4 Fibritin; Journal of Virology, May 2001, pp. 4176-4183.

Kugler et al.; Regression of human metastatic renal cell carcinoma after vaccination with tumor cell-dendritic cell hybrids; Nature Medicine, vol. 6, No. 3, Mar. 2000, pp. 332-336.

Kwak et al.; Induction of Immune Responses in Patients with B-Cell Lymphoma Against the Surface-Immunoglobulin Idiotype Expressed by Their Tumors; The New England Journal of Medicine, vol. 327, No. 17, pp. 1209-1215.

Lee et al.; Phenotype, Function, and In Vivo Migration and Survival of Allogeneic Dendrilic Cell Progenitors Genetically Engineered to Express TGF-β; Transplantation, vol. 66, pp. 1810-1817, No. 12, Dec. 27, 1998.

Lozier et al.; Adenovirus-Mediated Expression of Human Coagulation Factor IX in the Rhesus Macaque Is Associated With Dose-Limiting Toxicity; Blood, vol. 94, No. 12, Dec. 15, 1999, pp. 3968-3975.

Mathias et al.; Interactions of Soluble Recombinant Integrin αvβ5 with Human Adenoviruses; Journal of Virology, Nov. 17, 1998, pp. 8669-8675.

Mayordomo et al.; Bone Marrow-Derived Dendritic Cells Serve as Potent Adjuvants for Peptide-Based Antitumor Vaccines; Stem Cells 1997; 15:94-103.

Michael et al.; Addition of a short peptide ligand to the adenovirus fiber protein; Gene Therapy (1995) 2. 660-668.

Mittereder et al.; Evaluation of the Concentration and Bioactivity of Adenovirus Vectors for Gene Therapy; Journal of Virology, Nov. 1996, pp. 7498-7509.

Moll et al.; Designed heterodimerizing leucine zippers with a range of pIs and stabilities up to $10^{-13}$ M; Protein Science (2001), 10:649-655.

Morris et al.; Incorporation of an Isoleucine Zipper Motif Enhances the Biological Activity of Soluble CD40L (CD154); The Journal of Biological Chemistry, vol. 274, No. 1, Issue of Jan. 1, pp. 418-423, 1999.

Murphy et al.; Phase II Prostate Cancer Vaccine Trial: Report of a Study Involving 37 Patients with Disease Recurrence Following Primary Treatment; The Prostate 39:54-59 (1999).

Nestle et al.; Vaccination of meanoma patients with peptide- or tumor lysate-pulsed dendritic cells; Nature Medicine, vol. 4, No. 3, Mar. 1998, pp. 328-332.

Okada et al.; Efficient Gene Delivery into dendritic Cells by Fiber-Mutant Adenovirus Vectors: Biochemical and Biophysical Research Communications 282, 173-179 (2001).

O'Neal et al.; Toxicological Comparison of E2o-Deleted and First-Generation Adenoviral Vectors Expressing $o_1$-Antitrypsin after Systemic Delivery; Human Gene Therapy 9:1587-1598 (Jul. 20, 1998).

O'Neal et al.; Toxicity Associated with Repeated Administration of First-Generation Adenovirus Vectors Does Not Occur with a Helper-Dependent Vector; Molecular Medicine 6(3): 179-195, 2000.

Pardoll; Cancer vaccines; Immunology Today, vol. 14, No. 6, 1993, pp. 310-316.

Parrot & Barry; Metabotically Biotinylated Gene Therapy Vectors; Molecular Therapy vol. 3, No. 5, May 2001, S165.

Pereboev et al.; Phage Display of Adenovirus Type 5 Fiber Knob as a Tool for Specific Ligand Selection and Validation, Journal of Virology, Aug. 2001, pp. 7107-7113.

Pullen et al.; High-Affinity Interactions of Tumor Necrosis Factor Receptor-Associated Factors (TRAFs) and CD40 Require TRAF Trimerization and CD40 Multimerization: Biochemistry, 1999, 38, 10168-10177.

Reo et al.; Adenoviruses Activate Human Dendritic Cells without Polarization toward a T-Helper Type I-Inducing Subsel; Journal of Virology, jDec. 1999, pp. 10245-10253.

Robbins & Kawakami; Human tumor antigens recognized by T cells, Current Opinion in Immunology 1996. 8:628-636.

Song et al.; Dendritic Cells Genetically Modified wtih an Adenovirus Vector Encoding the cDNA for a Model Antigen Induce Protective and Therapeutic Antitumor Immunity; Journal Exp. Medicine, vol. 186, No. 8, Oct. 20, 1997 1247-1256.

Specht et al.; Dendritic Cells Retrovirally Transduced with a Model Antigen Gene are Therapeutically Effective against Established Pulmonary Metastases; The Journal of Experimental Medicine, vol. 186, No. 8, Oct. 20, 1997 1213-1221.

Su et al.; CD154 Variant Lacking Tumor Necrosis Factor Homologous Domain Inhibits Cell Surface Expression of Wild-type Protein; The Journal of Biological Chemistry, vol. 276, No. 3, Issue of Jan. 19, pp. 1673-1676, 2001.

Tillman et al.; Maturation of Dendritic Cells Accompanies High-Efficiency Gene Transfer by a CD40-Targeted Adenoviral Vector; The Journal of Immunology, 1999.

Tillman et al.; Adenoviral Vectors Targeted to CD40 Enhance the Efficacy of Dendritic Cell-based Vaccination against Human Papillomavirus 16-induced Tumor Cells in a Murine Model; Cancer Research 60, 5456-5463, Oct. 1, 2000.

Timmerman & Levy; Dendritic Cell Vaccines for Cancer Immunotherapy; Ammu. Rev. Med. 1999, 50:507-29.

Tjoa et al.; Presentation of Prostate Tumor Antigens by Dendritic Cells Stimulates T-Cell Proliferation and Cytotoxicity; The Prostate 28:65-69 (1996).

Tsang et al.; Generation of Human Cytotoxic T Cells Specific for Human Carcinoembryonic Antigen Epitopes from Patients Immunized with Recombinant Vaccinia-CEA Vaccine; Journal of National Cancer Institute, vol. 87, No. 13, Jul. 5, 1995.

Von Seggern et al.; Complementation of a fibre mutant adenovirus by packaging cell lines stably expressing the adenovirus type 5 fibre protein; Journal of General Virology (1998) 79, 1461-1468.

Wickham et al.; Adenovirus targeted to heparan-containing receptors increases its gene delivery efficiency to multiple cell types; Nature Biotechnology, vol. 14, Nov. 1996.

Wickham et al.; Increased In Vitro and In Vivo Gene Transfer by Adenovirus Vectors Containing Chimeric Fiber Proteins; Journal of Virology, Nov. 1997, pp. 8221-8229.

Yee et al.; Adenovirus-Mediated Gene Transfer of Herpes Simplex Virus Thymidine Kinase in an Ascites Model of Human Breast Cancer; Human Gene Therapy 7:1251-1257 (Jun. 20, 1996).

Zeng, Sticky-End PCR: New Method for Subcloning; BioTechniques, vol. 25, No. 2 (1998), pp. 206-208.

Zitvogel et al.; Therapy of Murine Tumors with Tumor Peptide-pulsed Dendritic Cells: Dependence on T Cells, B7 costimulation, and T Helper Cell I-associated Cytokines; Journal Exp. Med. vol. 183 Jan. 1996 87-97.

* cited by examiner

| heptad # | 1 abcdefg | 2 abcdefg | 3 abcdefg | 4 abcdefg | 5 abcdefg | 6 abcdefg | 7 abcdefg | |
|---|---|---|---|---|---|---|---|---|
| E•E$_{34}$ | R | AAFLEKE | NTALRTE | VAELEKE | VGRCENI | | | SEQ ID NO: 1 |
| R•R$_{34}$ | R | AAFLEKE | NTALRTR | VAELRKR | VGRCRNI | | | SEQ ID NO: 2 |
| EE$_{12}$RR$_{345}$L | LEIE | AAFLERE | NTALETR | VAELRQR | VQRLRNR | VSQYRTR | YGPL | SEQ ID NO: 3 |
| RR$_{12}$EE$_{345}$L | LEIR | AAFLRQR | NTALRTE | VAELEQE | VQRLENE | VSQYETR | YGPL | SEQ ID NO: 4 |

SEQUENCE LISTING

<160> NUMBER OF SEQ ID NOS: 4

<210> SEQ ID NO 1
<211> LENGTH: 29
<212> TYPE: PRT
<213> ORGANISM: Artificial Sequence
<220> FEATURE:
<221> NAME/KEY: PEPTIDE
<223> OTHER INFORMATION: zipper peptide E E34

<400> SEQUENCE: 1

Arg Ala Ala Phe Leu Glu Lys Glu Asn Thr Ala Leu Arg Thr Glu
                5                  10                 15
Val Ala Glu Leu Glu Lys Glu Val Gly Arg Cys Glu Asn Ile
            20                  25

<210> SEQ ID NO 2
<211> LENGTH: 29
<212> TYPE: PRT
<213> ORGANISM: Artificial Sequence
<220> FEATURE:
<221> NAME/KEY: PEPTIDE
<223> OTHER INFORMATION: zipper peptide R R34

<400> SEQUENCE: 2

Arg Ala Ala Phe Leu Glu Lys Glu Asn Thr Ala Leu Arg Thr Arg
                5                  10                 15
Val Ala Glu Leu Arg Lys Arg Val Gly Arg Cys Arg Asn Ile
            20                  25

```
<210> SEQ ID NO 3
<211> LENGTH: 43
<212> TYPE: PRT
<213> ORGANISM: Artificial Sequence
<220> FEATURE:
<221> NAME/KEY: PEPTIDE
<223> OTHER INFORMATION: zipper peptide EE12RR345L

<400> SEQUENCE: 3

Leu Glu Ile Glu Ala Ala Phe Leu Glu Arg Glu Asn Thr Ala Leu
                 5                  10                  15

Glu Thr Arg Val Ala Glu Leu Arg Gln Arg Val Gln Arg Leu Arg
             20                  25                  30

Asn Arg Val Ser Gln Tyr Arg Thr Arg Tyr Gly Pro Leu
             35                  40

<210> SEQ ID NO 4
<211> LENGTH: 43
<212> TYPE: PRT
<213> ORGANISM: Artificial Sequence
<220> FEATURE:
<221> NAME/KEY: PEPTIDE
<223> OTHER INFORMATION: zipper peptide RR12EE345L

<400> SEQUENCE: 4

Leu Glu Ile Arg Ala Ala Phe Leu Arg Gln Arg Asn Thr Ala Leu
                 5                  10                  15

Arg Thr Glu Val Ala Glu Leu Glu Gln Glu Val Gln Arg Leu Glu
             20                  25                  30

Asn Glu Val Ser Gln Tyr Glu Thr Arg Tyr Gly Pro Leu
             35                  40
```

ADENOVIRAL VECTOR INCORPORATING ZIPPER PEPTIDE-MODIFIED FIBER PROTEIN AND USES THEREOF

CROSS-REFERENCE TO RELATED APPLICATION

This non-provisional patent application claims benefit of provisional patent application U.S. Ser. No. 60/397,951, filed Jul. 22, 2002, now abandoned.

BACKGROUND OF THE INVENTION

1. Field of the Invention

The present invention relates generally to the field of immunotherapy. More specifically, the present invention relates to using zipper peptide-modified fiber protein to target adenoviral vectors for uses in immunotherapy.

2. Description of the Related Art

The repertoire of anti-cancer strategies, which have traditionally included surgery, chemo- and radiotherapy, has recently been expanded by the employment of novel therapeutic approaches such as anti-cancer vaccination. The rationale for the development of this new treatment modality is based on convincing evidence from studies in both laboratory animals (1–4) and humans (5–7) that the immune system can recognize and destroy malignant cells. The ultimate goal of vaccination in human cancer is to achieve long-lasting, tumor-specific immunologic memory characterized by a high destructive potential and specificity, resulting in tumor eradication in the patient.

The development of anti-cancer vaccination strategies has been rationalized by the recent identification of tumor associated antigens (TAA) which may be recognized by the immune system as specific markers of cancer cells, thereby identifying these cells as the targets. These tumor associated antigens include proteins encoded by genes with mutations or rearrangements unique to tumor cells, reactivated embryonic genes, tissue-specific differentiation antigens, and a number of other self proteins (8–15). However, despite the identification of these targets, development of effective anti-cancer vaccination strategies has been limited to a large extent by the lack of means for successful vaccination against these weak, self-derived antigens. The generation of a potent anti-tumor associated antigens immune response is thus recognized as a key issue in the development of efficient anti-cancer immunization strategies.

The problem of poor immunogenicity of self-derived tumor-associated antigens can be overcome by efficient antigen presentation by dendritic cells. Current understanding of the mechanisms of immune response development suggests that efficient capture and presentation of tumor associated antigens by antigen presenting cells (APCs) is a pivotal step in eliciting strong anti-cancer immunity. In this regard, dendritic cells (DCs), so-called "professional" antigen presenting cells, play a major role in the induction of an immune response due to their ability to process and present antigen, express high levels of co-stimulatory molecules, and activate both CD4+ and CD8+ naïve T lymphocytes (16).

Dendritic cells represent a heterogeneous population of bone marrow-derived cells present at low numbers in most peripheral tissues, where they continuously sample the antigenic content of their environment by phagocytosis, macropinocytosis and receptor-mediated endocytosis. A captured antigen is then processed intracellularly, being degraded into short peptides that are loaded onto class I and class II major histocompatibility (MHC) molecules for subsequent display on the cell surface. When dendritic cells encounter local inflammatory mediators, such as tumor necrosis factor α (TNFα) or bacterial lipopolysaccharide, they become activated and undergo a series of physiologic changes leading to their terminal differentiation, a process called "dendritic cell maturation".

Dendritic cell maturation includes redistribution of MHC molecules from intracellular endocytic compartments to the cell surface, a selective decrease of antigen and pathogen internalization activity and a marked increase in surface expression of co-stimulatory molecules for T cell activation. Maturation also entails profound changes in dendritic cell morphology, reorganization of their cytoskeleton and surface expression of several integrins and chemokine receptors that determine their migration from peripheral tissues to secondary lymphoid organs. Thus, dendritic cells serve as initiators of immune response, capturing antigen at portals of entry and delivering it in a highly immunogenic form for efficient display to T cells.

Stemming from their key function as central mediators of T cell-based immunity, the use of dendritic cells has been proposed in a number of clinical immunotherapy strategies. One of these strategies is based on the fact that immature dendritic cells present at their surface a large proportion of empty MHC class II molecules that disappear upon maturation. If these empty receptors are loaded ("pulsed") in vitro with tumor associated antigen-specific peptides, they can then stimulate T cells. Data obtained in several animal models have demonstrated that dendritic cells pulsed with synthetic peptides corresponding to known tumor antigens or tumor-eluted peptides are capable of inducing antigen-specific cytotoxic lymphocyte (CTL) responses that lead to protection from tumor challenge and, in some instances, regression of established tumors (17, 18). The same strategy has also been tested in human clinical trials with encouraging results. Importantly, comparable cytotoxic lymphocyte activity and tumor protection have been elicited using protein-pulsed dendritic cells (16, 19, 20).

An alternative approach uses dendritic cells that are transduced with antigen-encoding cDNA or RNA rather than tumor associated antigens (TAA) themselves or tumor associated antigens-derived peptides. Such gene-modified dendritic cells offer several potential advantages over peptide- or tumor associated antigens-loaded dendritic cells. Antigenic peptides are produced by these transduced dendritic cells themselves, loaded onto and presented by MHC molecules possibly within multiple MHC alleles, and multiple and/or undefined epitopes are potentially presented. Antigenic peptides are continuously produced and loaded onto MHC molecules in transduced dendritic cells, whereas in peptide-pulsed dendritic cells only a small proportion of cell surface MHC molecules are loaded with synthetic peptide. Furthermore, cDNA encoding immuno-modulators like, for example, cytokines and chemokines can be cotransfected in addition to antigen cDNA to affect dendritic cell and T cell functions, and to modulate immune responses. Remarkably, vaccination with dendritic cells pulsed with tumor associated antigen-encoding RNA or tumor-cell-derived polyadenylated RNA can induce CTL and protective tumor immunity (21). However, traditional physical (i.e. electroporation) or chemical (e.g. cationic lipids or calcium phosphate precipitation) methods of transfection with nucleic acids have proven either ineffective or too toxic for delivery of genes into dendritic cells (16).

In order to increase the efficiency of delivery of tumor associated antigen-encoding genes to dendritic cells, natural mechanisms of virus-mediated transduction of cells have been employed. To this end, recombinant viral vectors have proved to be more efficient in delivering tumor associated antigen-encoding sequences into dendritic cells than traditional transfection methods. Retrovirus and adenovirus (Ad) vectors coding for model tumor antigens have been used to infect dendritic cells and induce both protective and therapeutic tumor immunity (2, 3, 21). However, retroviral vectors require proliferating cells for efficient infection and are characterized by a limited capacity to accommodate heterologous DNA. In addition, retroviral vectors are difficult to produce in amounts sufficient for extensive therapeutic use. In contrast, adenovirus vectors can infect both dividing and non-dividing cells, can incorporate a substantial amount of foreign DNA, and are easily propagated and purified. This set of attractive features suggests that adenoviral vectors may be a more efficient mean of dendritic cell transduction.

Several years of studies employing adenoviral vectors for transduction of dendritic cells, however, have resulted in rather controversial data on the efficiency of this method. A critical analysis of the literature reveals that in those instances where significant levels of adenoviral-mediated gene transfer to dendritic cells was reported, very high multiplicities of infection (MOIs) had to be used. For instance, Dietz et al. reported adenoviral-mediated gene transfer to human dendritic cells using an adenoviral vector only at a MOI of 5,000 virions per cell (22). Similarly, in order to achieve efficient transduction of bone marrow-derived murine dendritic cells with Ad, Kaplan et al. used an MOI of 500 infection units per cell (23), and Rea et al. transduced human dendritic cells at a MOI of 1,000 plaque forming units per cell (24). Whereas the need to use such high doses of the vector does not normally constitute a problem in "proof of concept" studies done in a laboratory, it prevents broad application of adenoviral-transduced dendritic cells as therapeutic vaccines in the clinic. Importantly, the exposure of immature dendritic cells, whose primary biological function is to capture antigen, to a high concentration of adenoviral vectors may result in the capture of adenoviral virions by the dendritic cells and elicitation of an anti-adenoviral rather than the desired anti-tumor associated antigen immune response expected from the transduction. While these considerations may not present problems with respect to ex vivo immunization of dendritic cells with adenoviral vectors, they are particularly important in the context of potential application of adenoviral-mediated transduction of dendritic cells in vivo, where high doses of adenoviral vectors administered to patients may cause severe side effects due to toxicity (25–29), thereby compromising the efficiency of the treatment. Thus, any significant improvement on adenoviral vectors' capacity to transduce dendritic cells that would allow utilization of lower viral doses with higher rates of gene transfer would be highly beneficial for the field of genetic immunization.

Recent studies designed to address the resistance of dendritic cells to adenoviral infection have revealed the molecular basis of this problem. A majority of human adenoviruses utilize a cell entry pathway that involves the primary cellular receptor, the coxsackie virus and adenovirus receptor (CAR). Expression of CAR below certain threshold levels may be a common reason for the adenoviral-refractoriness of a variety of cell targets (30). Specifically, poor efficiencies of gene transfer to dendritic cells by adenoviral vectors have been shown to correlate with low levels of CAR expression in these cells (24, 31–33). Therefore, the dependence of adenoviral-mediated transduction on the levels of CAR expressed on target dendritic cells represents a major obstacle in using adenoviral vectors for genetic immunization.

CAR-deficiency of dendritic cells and their refractoriness to adenoviral infection may be overcome by modification of adenoviral tropism to target the vector to specific receptors expressed by dendritic cells. Recent studies performed at the Gene Therapy Center at University of Alabama at Birmingham have clearly demonstrated the efficacy of this tropism modification strategy by targeting the vector to the CD40 receptor present on the surface of dendritic cells. Specifically, by employing a bispecific antibody with affinities for both the adenovirus fiber knob and CD40, a luciferase-expressing adenoviral vector was re-routed via CD40 that served the role of an alternative primary receptor for adenoviral binding. The selection of CD40 as an alternative receptor for the adenoviral vector was rationalized by the fact that this molecule, which play an important role in antigen-presentation by dendritic cells, is efficiently expressed by immature dendritic cells (16). The CD40-targeted adenoviral vector increased reporter gene expression in dendritic cells by at least two orders of magnitude as compared to untargeted Ad. Furthermore, this enhancement was blocked by ~90% when cells were pretreated with an excess of the unconjugated anti-CD40 monoclonal antibody.

Importantly, this antibody-based targeting resulted in modulation of the immunological status of dendritic cells by inducing their maturation. This was demonstrated phenotypically by increased expression of CD83, MHC, and costimulatory molecules, as well as functionally by production of IL-12 and an enhanced allostimulatory capacity in a mixed lymphocyte reaction (MLR). It has been reported that activation of dendritic cells to maturity renders them resistant to the effects of dendritic cell inhibitory cytokines like IL-10 (34) as well as to direct tumor-induced apoptosis. The capacity with which murine dendritic cells can generate an immune response in vivo has been shown to correlate with the degree of their maturation (35). Moreover, based on proposals that CD40 activation may bypass $CD4^+$ T cell help (33), a CD40-targeted adenoviral might also have applications in cases of $CD4^+$ dysfunction. The dual role of CD40 in this schema as both a surrogate adenoviral receptor and a powerful trigger of dendritic cell maturation rationalizes further development of dendritic cell-targeting adenoviral vectors for anti-cancer immunization.

However, there is a clear need for further improvements in targeted adenoviral vectors for dendritic cell-based anti-cancer vaccination. Despite the significant advantages offered by a CD40-specific adenoviral vector targeted to dendritic cells by a bispecific antibody, the large-scale production of targeting bispecific antibody appears to be a major hurdle in the development of this technology. Not only does the production of these conjugates require the manufacture of two individual antibodies constituting the conjugate, it also necessitates efficient conjugation of the antibodies to generate a high yield of functional product. As chemical conjugation of antibodies occurs in a random manner, a significant proportion of the cross-linked antibodies loses their antigen-binding capacity. The elimination of such non-functional by-products from the conjugation reaction further complicates the entire technological scheme and decreases the yield of the desired product, thereby increasing its cost. In addition, standardization for the production of bispecific antibody is not trivial, which makes it less attractive as a means to improve Ad-based immunization of dendritic cells in the clinic. Furthermore, additional purification steps are required in order to remove from the vector preparation excessive antibodies that do not bind to adenoviral virions and may otherwise work as inhibitors of targeted gene transfer.

Thus, the prior art is deficient in methods of targeting adenoviral vectors to dendritic cells for efficient adenoviral-based immunization of dendritic cells. The methodology described in the present invention fulfills this long-standing need and desire in the art by making and using CD40-targeted adenoviral vectors containing zipper-modified fiber protein.

SUMMARY OF THE INVENTION

The present invention is directed to a targeted recombinant adenovirus vector comprising (i) a gene encoding a heterologous protein; (ii) a modified fiber protein with a first zipper peptide inserted at the HI loop or the carboxy terminal of a fiber protein, or at the carboxy terminus of a fiber-fibritin protein chimera; and (iii) a gene encoding a fusion protein comprising a second zipper peptide and a targeting ligand. Binding of the first zipper peptide to the second zipper peptide would connect the targeting ligand to the modified fiber protein, thereby targeting the adenovirus vector to a cell that expresses a cell surface molecule that binds to the targeting ligand.

The present invention is also directed to a method of gene transfer to CD40+ cells using the CD40-targeted adenoviral vector disclosed herein. In general, the CD40+ cells are dendritic cells.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. The appended drawings illustrate preferred embodiments of the invention and therefore are not to be considered limiting in their scope.

FIG. 1 shows a schematic representation of a parallel dimeric coiled coil (leucine zipper). FIG. 1B shows the side view of the dimer. The helical backbones are represented by cylinders, and the knobs represent the side chains. The path of the polypeptide chain is indicated by a line wrapped around the cylinders. Gray bars indicate interhelical interactions.

FIG. 4 shows a scheme of rescue and propagation for zipper-modified adenoviral vector. To facilitate plaque formation by the modified adenoviruses during the rescue of the virus, cells that constitutively express wild type fiber are transfected with the recombinant adenoviral genome derived in E. coli. Rescued viruses are then propagated in these cells to provide enough viral material for large-scale infection of 293 cells, which results in homogeneous population of virions containing zipper-modified fibers.

FIG. 5 shows the expression and functional validation of recombinant form of soluble CD40L (sCD40L) protein. FIG. 5B: The ability of sCD40L to bind CD40 was demonstrated in a FACS assay. 293 cells (CD40-negative) and 293/CD40 cells that constitutively express cell surface-localized human CD40 (derived at the Gene Therapy Center at University of Alabama) were probed with sCD40L, followed by a FITC-conjugated anti-6His mAb. Cells incubated with the secondary antibody only served as a negative control of binding.

DETAILED DESCRIPTION OF THE INVENTION

The aforementioned technological problems associated with targeting adenoviral vector with bispecific antibody could be obviated by the generation of a single-component adenoviral vector capable of binding to CD40 expressed on dendritic cells. For instance, the tropism of such a vector could be modified by cross-linking a recombinant form of an anti-CD40 monoclonal antibody (mAb) to the adenoviral capsid, thereby directing the virus to CD40. Importantly, a single-chain (scFv) version of anti-human CD40 monoclonal antibody G28.5 has been derived at the Gene Therapy Center at University of Alabama (36) and its ability to bind CD40 expressed on cell surface has been demonstrated (37). As this scFv represents the CD40-binding domains of the parental monoclonal antibody, by all accounts it should retain the capacity of G28.5 to activate dendritic cells upon binding to CD40 and may thus be used as an adequate substitute for the full size monoclonal antibody in a targeting strategy.

Alternatively, an adenoviral vector may be targeted to CD40 by cross-linking with the natural ligand for CD40 receptor, CD40 Ligand or CD40L. CD40–CD40L interaction is characterized by high affinity and specificity and also launches a cascade of events leading to the initiation of an immune response. The multivalent interaction of trimeric CD40L with CD40 receptors causes CD40 ligation, which then results in enhanced survival of these cells and secretion of cytokines such as IL-1, IL-6, IL-8, IL-10, IL-12, TNF-α, MIP-1a and enzymes such as matrix metalloproteinase. CD40–CD40L interaction also enhances monocyte tumoricidal activity. In addition, ligation of CD40 to CD40L considerably alters dendritic cell phenotype by upregulating the expression of costimulatory molecules such as CD54/ICAM-1, CD58/LFA-3, CD80/B7-1, and CD86/B7-2. Therefore, the interaction between CD40 and CD40L has important consequences for both antigen presenting cell function and T cell function.

Since both targeting ligands originate from molecules which normally are expressed in either a cell surface-localized (CD40L) or secretory (G28.5) form, their biosynthesis should follow the natural biosynthetic pathways of the parental molecules. This is crucial for the correct posttranslational modification of the ligands to ensure their proper functioning. In essence, this may be achieved by the derivation of an adenoviral vector system which would allow independent synthesis and assembly of its individual components—the targeting ligand, CD40L or anti-CD40 scFv, and the adenoviral virion—prior to their association. Functional configurations of the ligand and the vector may then be retained in the context of the final targeting complex by using a cross-linking mechanism which does not compromise the functions of either component.

Figure 1A:
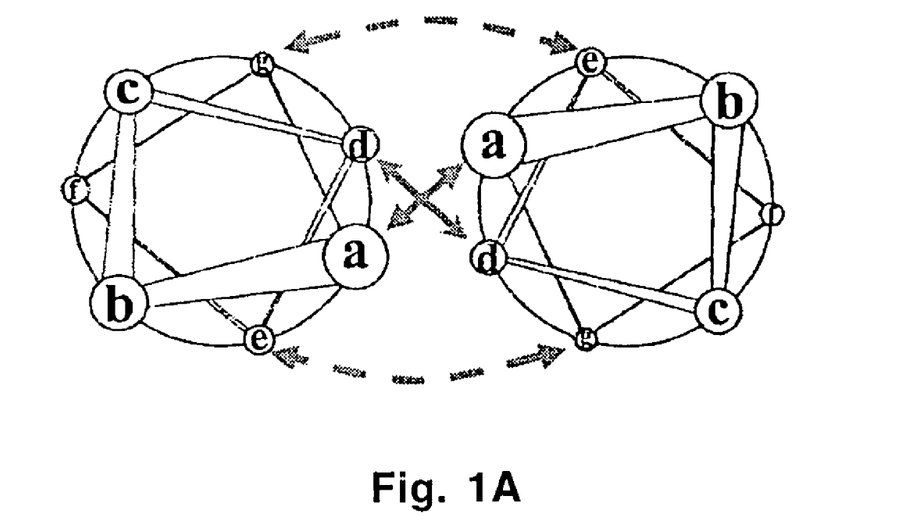
FIG. 1A shows zipper dimer visualized from the amino terminus illustrating inter-helical interactions and hydrophobic core formed by the a- and d-positions.
Figure 1B:
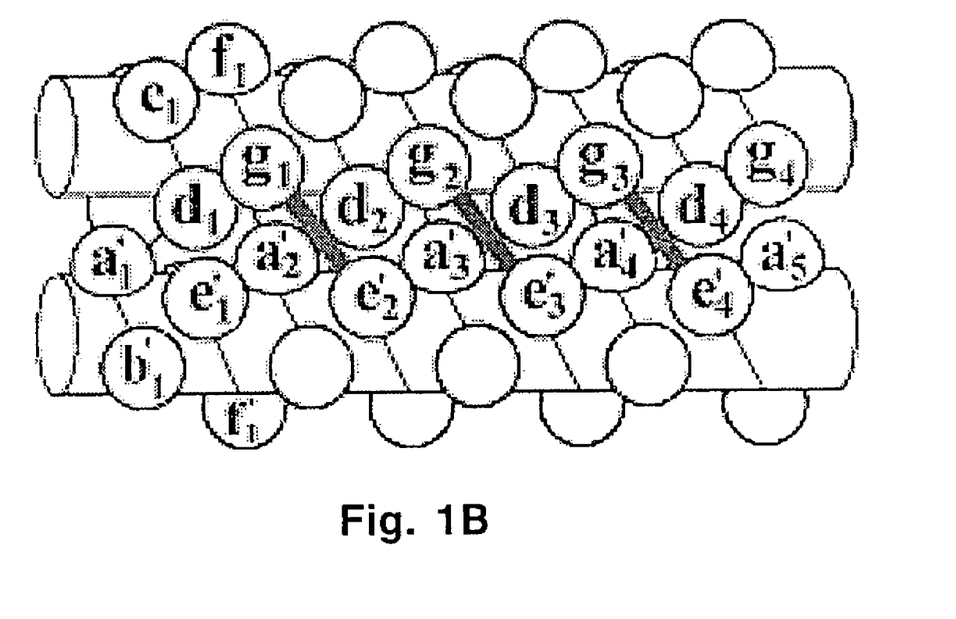
Figure 2:
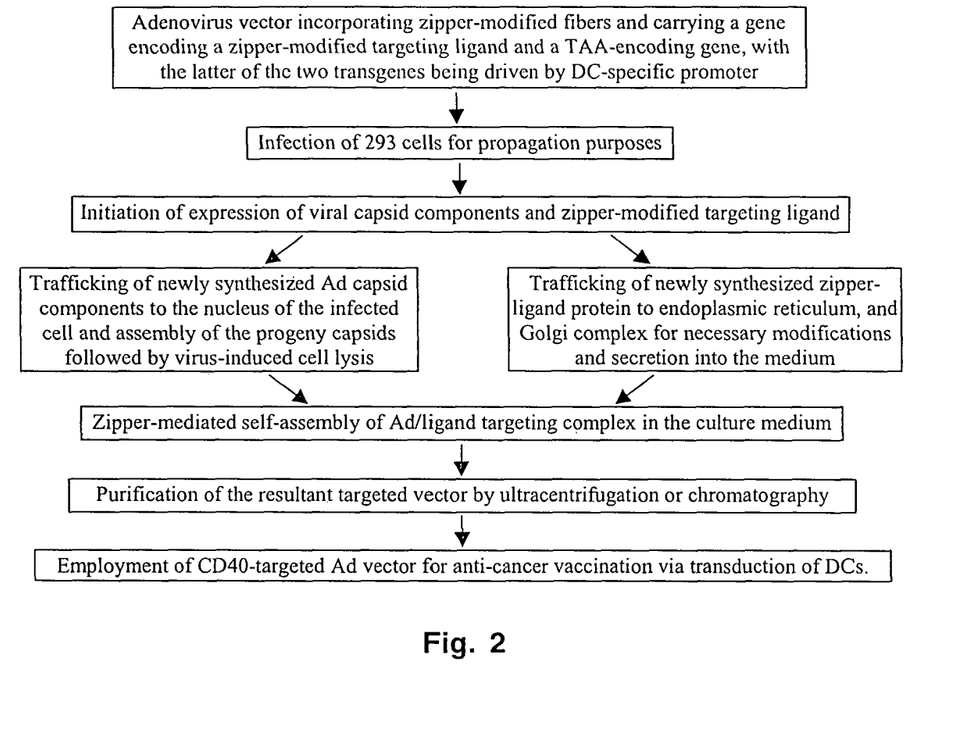
FIG. 2 shows a technological scheme for the generation of a CD40-targeted adenoviral vector for genetic vaccination via transduction of dendritic cells.

The problem of generating functional two-component complexes has been successfully addressed previously by employing so-called "peptide zippers". These zippers normally consist of two peptides capable of associating in heteroduplexes via formation of so-called coiled coils. Dimeric coiled-coils consist of two amphipathic helices wrapping around each other with a slight supercoil. They contain a characteristic heptad repeat $(a-b-c-d-e-f-g)_n$ with a distinct pattern of hydrophobic and hydrophilic residues (38, 39). The positions a and d, which form the hydrophobic interface between the helices, are usually aliphatic and have a profound effect on the oligomerization state. The positions b, c, e, g, and f are solvent-exposed and usually polar. The positions e and g, which flank the hydrophobic core, can make interhelical interactions, and thereby mediate heterospecific pairing (FIG. 1). Despite the short length of typical peptide zippers (25–50 aa) they are highly stable. Furthermore, based on the well-understood mechanisms of coiled-coil formations, a number of strategies have been proposed to improve the stability of the duplexes as well as to avoid the formation of homoduplexes while favoring heterodimers. Representative examples of such tailor-designed peptide zippers have been described in the papers by Moll et al. (40) and Arndt et al. (41).

In order to link two components by the peptide zippers technique, each moiety constituting the duplex is genetically fused with a peptide zipper and then the two complementary zipper-containing constituents are allowed to associate either in vitro or in vivo. The practical utilization of peptide zippers in the construction of two-component complexes has been successfully demonstrated for the association of the α and β chains of recombinant integrin $α_vβ_5$ (42). In that study, the two subunits of the integrin molecule, expressed as individual polypeptides deleted for their transmembrane domains, were linked via a peptide zipper, resulting in the formation of a functional heterodimer of soluble integrin. Katz et al. demonstrated a successful self-association of zipper-containing green fluorescent protein (GFP) and α-actinin in mammalian cells, thereby illustrating the possibility of zipper-mediated formation of heterologous protein complexes in vivo (43). Recent work by Pereboev et al. (44) described the use of peptide zippers to link filamentous bacteriophage particles and recombinant Ad5 fiber knob proteins expressed by the phages. Due to the structural incompatibility of the fiber knob with the phage coat proteins, which are normally used for ligand presentation, the only way to link these two components together was via a peptide zipper. This work demonstrated the feasibility of zipper-mediated linkage of extraneous proteins to viral particles. Thus, it appears to be feasible to use peptide zippers to link recombinant CD40-specific ligands to genetically modified capsids of adenoviral vectors.

One object of the present invention is to develop a new adenoviral vector system targeted to human dendritic cells via utilization of CD40 as an alternative viral receptor. This vector in its final configuration will consist of a recombinant form of either CD40L or an anti-CD40 scFv linked via a peptide zipper to an adenoviral virion encoding a specific tumor associated antigen, wherein both the virion and the ligand will incorporate one of the two peptides constituting the linking zipper. Importantly, the zipper-containing ligand will be encoded by the genome of the same adenoviral vector it is supposed to associate with and thus retarget. This feature would greatly facilitate large-scale manufacturing of the targeted vector by eliminating the need for production of the vector and the targeting ligand in two separate technological processes.

The success of the adenoviral targeting approach disclosed herein depends on the generation of a recombinant adenoviral fiber molecule incorporating a zipper peptide that does not compromise the correct folding of the entire fiber-zipper chimera. Of note, for efficient association with the penton base protein and incorporation into mature adenoviral particle, the fiber-zipper should retain trimeric configuration of the wild type fiber. In addition, the fiber-zipper chimera needs to have a configuration that allows for efficient interaction between the zipper peptide attached to the fiber and its partner peptide attached to a targeting ligand. To date, the carboxy terminus and the HI loop within the fiber knob domain have been identified as favoring incorporation of heterologous peptide sequences (45–49). Of note, the most recent work has demonstrated that each of these sites within the fiber can accommodate polypeptide sequences exceeding 70 amino acid residues in length (50, 51). The present invention capitalizes on these findings and introduces peptide sequences constituting zipper duplexes into these sites within the fiber molecule. The resultant fiber-zipper proteins can be transiently expressed in mammalian cells and their ability to assemble into homotrimers can be confirmed. Furthermore, those fiber-zipper chimeras capable of self-trimerization can then be tested for the capacity to be incorporated into fiber-deleted adenoviral virions.

In addition to modifying the Ad fiber protein with zipper peptide, the fiber-fibritin chimera can be employed as an alternative strategy to generate the fiber-zipper chimeric protein. The fiber-fibritin protein was designed so that the structure of the domain providing for trimerization of the chimera (fibritin) is not affected by incorporation of heterologous peptides/polypeptides within the protein, thereby dramatically increasing the odds of obtaining stable derivatives of this "backbone" molecule. This strategy of fiber replacement has been described in a recent paper (60).

In view of the present disclosure, one of ordinary skill in the art would readily apply the method of the instant invention to direct adenoviral vectors carrying various heterologous proteins to targets besides CD40. Representative examples of targeting ligands include CD40 ligand, a single chain fragment (scFv) of anti-human CD40 antibody, fibroblast growth factor, epidermal growth factor and somatostatin. Representative examples of the heterologous protein include tumor associated antigens, HER2/neu and carcinoemryonic antigen.

As used herein, the term "zipper peptide" refers to two peptides capable of associating in heteroduplexes via formation of so-called coiled coils.

In accordance with the present invention there may be employed conventional molecular biology, microbiology, and recombinant DNA techniques within the skill of the art.

Such techniques are explained fully in the literature. See e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The term antibody used herein is intended to encompass both polyclonal and monoclonal antibodies. The term antibody is also intended to encompass whole antibodies, biologically functional fragments thereof, chimeric and humanized antibodies comprising portions from more than one species.

Biologically functional antibody fragments include Fab, Fv, F(ab')$_2$, and scFv (single-chain antigen-binding protein) fragments. As used herein, single chain antibodies or scFvs are polypeptides which consist of the variable (V) region of an antibody heavy chain linked to the V region of an antibody light chain with or without an interconnecting linker. This comprises the entire antigen binding site, and is the minimal antigen binding site.

Chimeric antibodies can comprise proteins derived from two different species. The portions derived from two different species can be joined together chemically by conventional techniques or can be prepared as a single contiguous protein using genetic engineering techniques (See, e.g., Cabilly et al., U.S. Pat. No. 4,816,567, Neuberger et al., WO 86/01533 and Winter, EP 0,239,400). Such engineered antibodies can be, for instance, complementarity determining regions (CDR)-grafted antibodies (Tempest et al., *Biotechnology* 9:266–271 (1991)) or "hyperchimeric" CDR-grafted antibodies which employ a human-mouse framework sequence chosen by computer modeling (Queen et al., *Proc. Natl. Acad. Sci. USA* 86:10029–10033 (1989)).

The present invention is directed to a targeted recombinant adenovirus vector comprising (i) a gene encoding a heterologous protein; (ii) a modified fiber protein with a first zipper peptide inserted at the HI loop or the carboxy terminal of a fiber protein, or at the carboxy terminus of a fiber-fibritin protein chimera; and (iii) a gene encoding a fusion protein comprising a second zipper peptide and a targeting ligand. Binding of the first zipper peptide to the second zipper peptide would connect the targeting ligand to the modified fiber protein, thereby targeting the adenovirus vector to a cell that expresses a cell surface molecule that binds to the targeting ligand. Representative examples of useful zipper peptides include peptides having the sequences of SEQ ID No. 1, 2, 3, or 4. In one embodiment of the present invention, the adenovirus vector is targeted to CD40$^+$ cells, such as dendritic cells, by employing CD40 ligand or a single chain fragment (scFv) of anti-human CD40 antibody as targeting ligand.

The present invention is also directed to a method of gene transfer to CD40$^+$ cells using the CD40-targeted adenoviral vector disclosed herein. In general, the CD40$^+$ cells are dendritic cells.

The following examples are given for the purpose of illustrating various embodiments of the invention and are not meant to limit the present invention in any fashion.

EXAMPLE 1

Generation of Fiber-Zipper Genes

Figure 3:
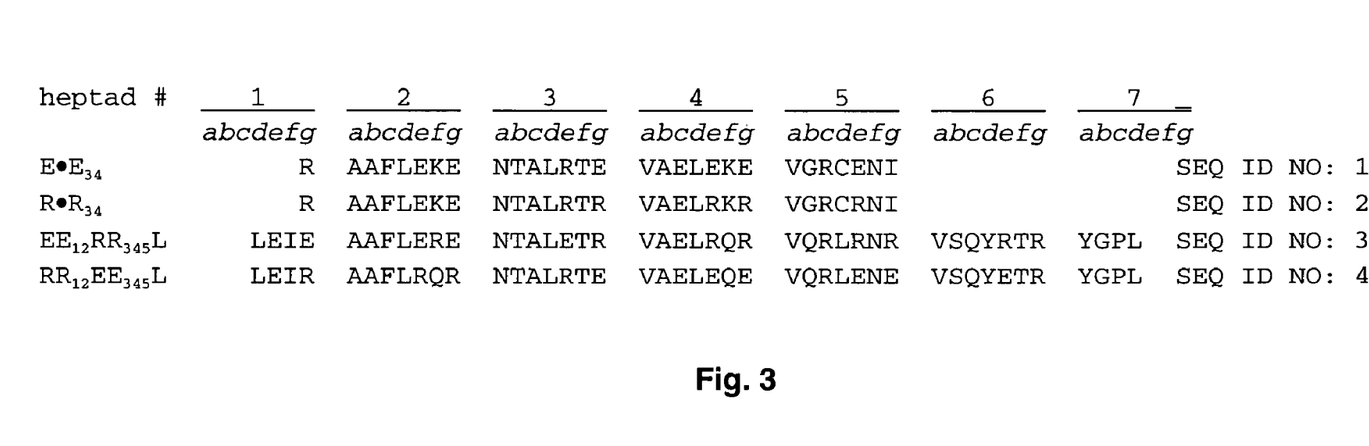
FIG. 3 shows candidate pairs of zipper peptides to be used for cross-linking targeting ligands with adenoviral virions. Peptides $E.E_{34}$ (Seq. ID No. 1) and $R.R_{34}$ (Seq. ID No. 2) have been used by Katz et al. for intracellular cross-linking of GFP and a-actinin (43), while the structure of the peptides $EE_{12}RR_{345}L$ (Seq. ID No. 3) and $RR_{12}EE_{345}L$ (Seq. ID No. 4) was optimized to increase the stability of heteroduplex and also to destabilize homodimers (40).

The genes encoding the fiber-zipper proteins were assembled in the pVS1 and pVS2 mammalian expression vectors which have been designed to facilitate the generation of genes encoding fiber proteins modified at the carboxy terminus or within the HI loop, respectively. Sequences coding for each of the four peptides comprising the two zippers shown in FIG. 3 were assembled with oligonucleotides and cloned into unique BaeI-sites engineered in pVS1 and pVS2. Also, a modified fiber protein containing additional peptide linkers within the HI loop was used as a carrier for zipper peptides. These peptides have also been incorporated into the carboxy terminus of a fiber-fibritin protein chimera previously designed by Krasnykh et al. (60). Therefore, a total of sixteen recombinant genes (four peptide zippers×four locales) have been generated (Table 1).

The fiber-fibritin chimera (60) was employed as an alternative strategy to generate the fiber-zipper chimeric gene. The fiber-fibritin protein has been designed so that the structure of the domain providing the trimerization of the chimera (fibritin) is not affected by incorporation of heterologous peptides/polypeptides within the protein, thereby increasing the odds of obtaining stable derivatives of this "backbone" molecule. The strategy of fiber replacement has been described recently (60). More importantly, the fiber-fibritin-zipper protein incorporating R.R$_{34}$ peptide has been shown to associate in a zipper-mediated manner with a recombinant form of green fluorescent protein (GFP) incorporating the complementary E.E$_{34}$ zipper peptide. This result clearly shows that the R.R$_{34}$ peptide contained within the fiber-fibritin-R.R$_{34}$ chimera is accessible and capable of binding with a partner containing the complementary zipper peptide.

TABLE 1

Expression Plasmids Encoding The Fiber-Zipper Chimeras

| Vector | Zipper | Modification within the HI loop | Modification at the carboxy terminus |
|---|---|---|---|
| pVS-HI-E | E-E$_{34}$ | + | |
| pVS-HI-R | R-R$_{34}$ | + | |
| pVS-HI-EN | EE$_{12}$RR$_{345}$L | + | |
| pVS-HI-RN | RR$_{12}$EE$_{345}$L | + | |
| pVS-PB40-E | E-E$_{34}$ | + | |
| pVS-PB40-R | R-R$_{34}$ | + | |
| pVS-PB40-EN | EE$_{12}$RR$_{345}$L | + | |
| pVS-PB40-RN | RR$_{12}$EE$_{345}$L | + | |
| pVS-LL-E | E-E$_{34}$ | | + |
| pVS-LL-R | R-R$_{34}$ | | + |
| pVS-LL-EN | EE$_{12}$RR$_{345}$L | | + |
| pVS-LL-RN | RR$_{12}$EE$_{345}$L | | + |
| pVS-FF-LL-E | E-E$_{34}$ | | + |
| pVS-FF-LL-R | R-R$_{34}$ | | + |
| pVS-FF-LL-EN | EE$_{12}$RR$_{345}$L | | + |
| pVS-FF-LL-RN | RR$_{12}$EE$_{345}$L | | + |

For transient expression of the fiber-zipper genes in mammalian cells, 293 cells were transfected with the newly constructed expression vectors to produce the proteins of interest. The ability of the fiber-zipper proteins transiently expressed in the transfected 293 cells to form homotrimers was analyzed by Western blot using an anti-fiber antibody. For this, cells were collected and lysed 72 hrs post transfection and soluble proteins were fractionated on SDS-PAGE gel. Each protein sample was loaded on the gel in both a completely denatured (boiling for 5 min) and a semi-native (no boiling) form. After electrotransfer onto a PVDF membrane, the blots were developed with anti-Ad5 fiber tail monoclonal antibody 4D2 (53). Wild type Ad5 fiber expressed in parallel was used as a positive control for trimerization. Transient expression of these fibers in mammalian cells shows that the vast majority of them were produced at levels comparable with that of the wild type Ad5 fiber and can form homotrimers (Table 2), a key structural property of the adenoviral fiber required for its successful association with an adenoviral virion.

To examine binding of the fiber-zipper proteins to the coxsackie virus and adenovirus receptor (CAR), lysates of plasmid-transfected cells were incubated with a soluble form of CAR, sCAR, which contains a carboxy terminal 6His tag (54). sCAR-containing complexes were isolated from the mixture by binding to Ni-NTA-matrix. The material bound to the resin were eluted with SDS-containing gel loading buffer and analyzed by SDS-PAGE. Fiber-zipper proteins co-precipitated with sCAR were detected with anti-fiber antibody. As shown in Table 2, at least six of the designed fiber proteins retain the ability to bind the native adenoviral receptor.

Figure 4:
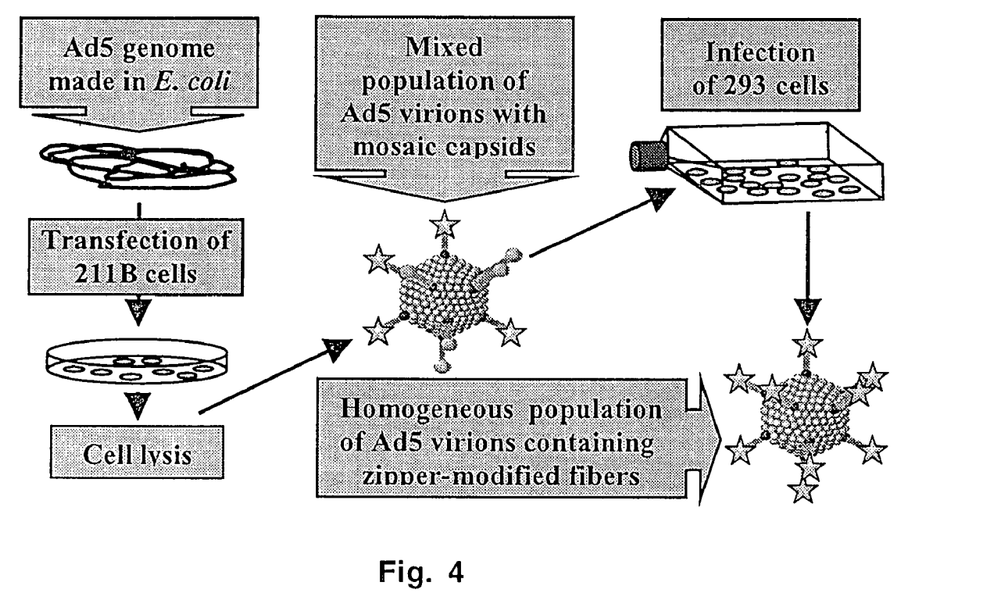

Lack of CAR binding per se does not constitute a problem in the context of the present invention, as the CD40-targeted vector to be developed should lack CAR tropism anyway. Failure of some of these molecules to bind CAR is not a concern, as the adenoviral vectors incorporating such fibers can be rescued in a two-step virus rescue/propagation scheme utilizing the fiber-complementing cell line described previously (60, 61) (FIG. 4). A cell line stably expressing wild type Ad5 fiber may be used for the rescue and propagation of CAR-ablated viruses. Wild type fiber proteins produced by such cells are incorporated into the capsids of adenoviral vectors amplified on these cells, thereby guaranteeing efficient rescue and subsequent reinfection of any CAR-positive cells. Therefore, after being rescued an adenoviral vector with ablated tropism for CAR may be propagated on these cells at any desirable scale. Ultimately, a preparation of such a vector devoid of wild type fiber proteins can be achieved by an additional round of propagation in 293 cells. The capsids of the resultant vectors will only contain modified fibers encoded by the viral genome. This approach was originally described by Von Seggern et al. (61) and has been used by Krasnykh et al. (60).

After the protein. chimeras has been constructed, it is important to determine whether the fiber-zipper proteins can be incorporated into an adenovirus. This property of the chimeras were examined by allowing them to be incorporated into the capsid of an adenoviral vector deleted for the fiber gene and thus unable to produce its own fiber. Briefly, the incorporation of the fiber-zipper proteins into adenoviral virions were examined by first transfecting 293 cells with the fiber-zipper-expressing pVS vectors and then infecting these cells 48 hrs post transfection with an Ad5 vector deleted for the fiber gene. This latter vector, which incorporates a luciferase reporter gene, is propagated on a wild type fiber-complementing cell line and thus contains wild type fibers that allow for efficient infection of the pVS plasmid-transfected 293 cells. If a functional fiber-zipper chimera is expressed by the pVS vector, this protein would be incorporated into the adenoviral virion. Plasmid vectors expressing no fiber or wild type Ad5 fiber were used as negative and positive controls respectively. As shown in Table 2, most of the modified fiber species have been successfully incorporated into adenoviral capsids.

TABLE 2

Summary Of The Results On Expression, Trimerization, Incorporation Into adenoviral Capsids And CAR Binding Of Zipper-Modified adenoviral Fibers

| Site of incorporation | Zipper | Expression* | Trimerization* | Incorporation into adenoviral virions* | CAR binding* |
|---|---|---|---|---|---|
| HI-loop | $E-E_{34}$ | + | ± | + | + |
|  | $R-R_{34}$ | ± | − | − | NT |
|  | $EE_{12}RR_{345}L$ | + | ± | − | NT |
|  | $RR_{12}EE_{345}L$ | + | ± | − | NT |
| Carboxy terminus of the fiber | $E-E_{34}$ | + | ± | + | ± |
|  | $R-R_{34}$ | + | ± | − | NT |
|  | $EE_{12}RR_{345}L$ | + | ± | + | − |
|  | $RR_{12}EE_{345}L$ | + | ± | + | − |
| Extended HI loop | $E-E_{34}$ | + | + | + | ± |
|  | $R-R_{34}$ | + | + | + | ± |
|  | $EE_{12}RR_{345}L$ | + | + | + | − |
|  | $RR_{12}EE_{345}L$ | + | + | + | ± |
| Carboxy terminus of the fiber-fibritin chimera | $E-E_{34}$ | + | + | + | − |
|  | $R-R_{34}$ | + | + | + | − |
|  | $EE_{12}RR_{345}L$ | + | + | NT | − |
|  | $RR_{12}EE_{345}L$ | + | + | NT | − |

*"+", positive result; "−", negative result; "±", intermediate result; "NT", not tested.

EXAMPLE 2

Derivation of Adenoviral Genomes Containing Fiber-Zipper Genes

The genes encoding the fiber-zipper engineered in the pVS series of mammalian expression vectors were transferred into the fiber shuttle vector pKAN3.1 for subsequent incorporation into a recombinant adenoviral genome. The resultant shuttle vectors were then used for homologous DNA recombination in E.coli with the rescue vector pVK700 that contains the Ad5 genome deleted for the fiber gene and incorporating a luciferase-expressing cassette in place of the E1 region. This was done by co-transforming the recombination-prone E.coli BJ5183 with both plasmid constructs as described previously (45, 46). The structure of the rescue plasmids containing the desired fiber gene-modified genomes can be validated by restriction enzyme analysis and partial DNA sequencing.

To rescue and propagate the fiber-modified adenoviral vectors, the adenoviral genomes engineered in the rescue vectors were excised from the plasmids by restriction digestion and used to transfect monolayers of 293 cells in order to rescue the viruses of interest. This transfection was expected to result in a cytopathic effect, indicating the development of a viral infection. The resultant viral progeny were propagated by sequential passaging on fresh 293 cells until a total of 108 cells were infected with each of the viral constructs. Viruses isolated from infected cells were purified by equilibrium centrifugation on CsC1 gradients as previously described (45, 46). The titer of viral particles in each preparation was determined by measuring the DNA and protein concentrations of the samples (55). Infectious titers were determined by a spot assay on 293 cells (56). Overall yields and infectious unit/particle ratios were used as measures of the viability of the viruses and compared to those typically obtained with E1-deleted adenoviral vectors containing wild type fibers. The presence of the fiber-zipper genes in the genomes of the rescued viruses can be confirmed by PCR and partial sequencing of the genomic DNA isolated from purified virions. Table 3 shows a summary of results on rescue of adenoviruses, indicating that most of the vectors of interest have been rescued.

TABLE 3

Summary Of The Results On Rescue And Purification Of Adenoviruses

| Adenovirus | Zipper | Current status |
| --- | --- | --- |
| Ad5.HI-E | $E-E_{34}$ | Rescue completed |
| Ad5.Fb-LL-E | $E-E_{34}$ | Rescue completed |
| Ad5.Fb-LL-EN | $EE_{12}RR_{345}L$ | Rescue completed |
| Ad5.Fb-LL-RN | $RR_{12}EE_{345}L$ | Rescue completed |
| Ad5.PB40-E | $E-E_{34}$ | Rescue completed |
| Ad5.PB40-R | $R-R_{34}$ | Rescue completed |
| Ad5.PB40-EN | $EE_{12}RR_{345}L$ | Rescue failed |
| Ad5.PB40-RN | $RR_{12}EE_{345}L$ | Rescue completed |
| Ad5.FF-LL-E | $E-E_{34}$ | Rescue completed |
| Ad5.FF-LL-R | $R-R_{34}$ | Rescue completed |
| Ad5.FF-LL-EN | $EE_{12}RR_{345}L$ | Rescue completed |
| Ad5.FF-LL-RN | $RR_{12}EE_{345}L$ | Rescue completed |

EXAMPLE 3

Engineering and Expression of Zipper-Tagged Ligand Proteins

Following the construction of zipper-tagged adenoviral vectors as described above, targeting zipper-ligand proteins capable of association with those adenoviral vectors are constructed next. Recent work (37, 57) in engineering recombinant CD40L suggests that functional fusion proteins incorporating the TNF-like domain of CD40L can be successfully expressed in heterologous systems. Based on these findings, it is expected that zipper-modified versions of sCD40L engineered in the present invention will retain the capacity for self-trimerization, binding to CD40 and association with the adenoviral vectors incorporating complementary zipper peptides. Similarly, successful expression of a functional G28.5-derived anti-CD40 scFv in bacterial cells (36) suggests that a zipper-modified version of this protein could also be produced in bacterial cells.

Figure 5A:
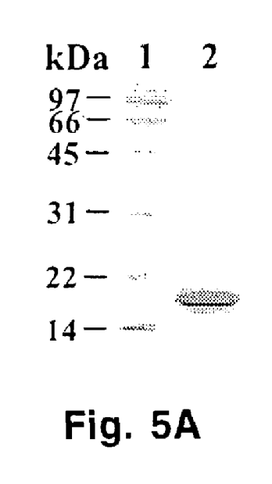
FIG. 5A: The carboxy terminal TNF-like domain of human CD40L was genetically fused with a 6His tag expressed in E. coli using the pET20b(+) plasmid (Novagen, Madison, Wis.), and purified using Ni-NTA-Sepharose (Qiagen, Valencia, Calif.). The resultant preparation was analyzed by SDS-PAGE. Lane 1, protein ladder (molecular masses shown in kilodaltons); lane 2, monomer of sCD40L protein (the sample was boiled for 5 min prior to loading on the gel).
Figure 5B:
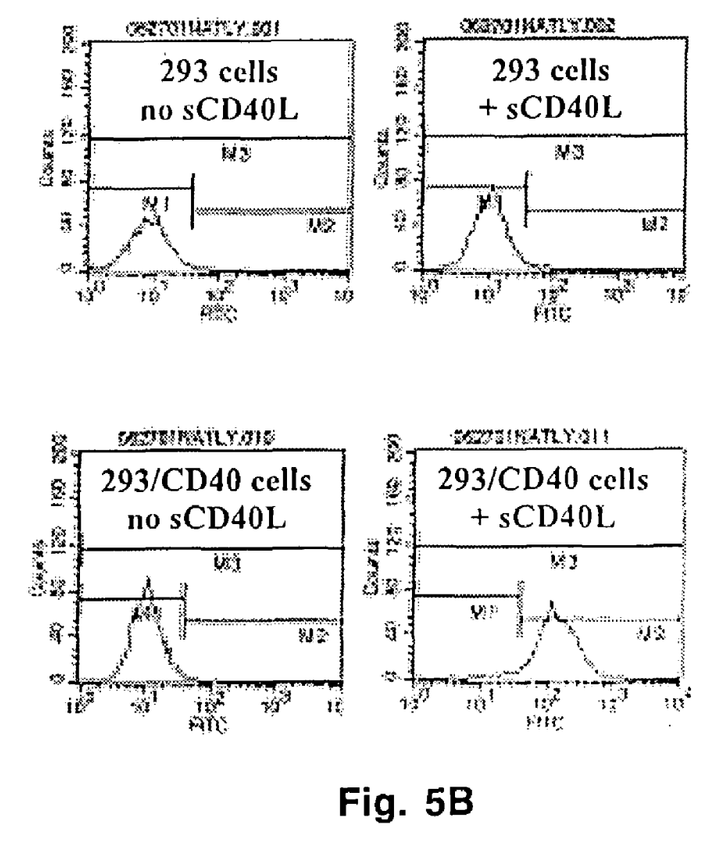

Peptides constituting zippers that pair with those incorporated into the adenoviral virions as disclosed in Example 2 are genetically fused to the amino termini of recombinant forms of either the TNF-like globular domain of human CD40L protein or an anti-CD40 scFv. At the zipper/ligand junction, a 6His tag is inserted to facilitate subsequent purification of the chimeras by immobilized metal ion affinity chromatography (IMAC). The genes encoding these fusion proteins are assembled by the "sticky end PCR" technique (58) and subsequently cloned into bacterial expression vectors of the pET series. Each fusion protein is expressed in E. coli and IMAC-purified for subsequent functional validation. This experimental scheme would result in efficient production of highly purified 6His-sCD40L proteins (20 mg of 95% pure sCD40L per liter of bacterial culture, FIG. 5A) that are capable of binding to cell surface CD40 (FIG. 5B).

An alternative way to obtain preparative amounts of zipper-ligand proteins is to express them in eukaryotic cells. This may be achieved by generating cell lines that stably express the desired proteins in secretory form. Such cell lines can be generated in a time- and labor-efficient manner by using the novel Flp-In™ system available from Invitrogen. This methodology capitalizes on high efficiency of integration of the expression vector of interest into a pre-determined site in the host cell genome, thereby eliminating the need for tedious isolation, propagation and characterization of individual clones. Moreover, and preferentially, secretory versions of zipper-ligand proteins can be transiently expressed in mammalian cells by recombinant adenoviral vectors. Of note, adenoviral vectors have been successfully used to express a number of secretory proteins, including 6His-tagged sCD40L (37). This approach will result in higher expression of the proteins.

If incorporation of peptide zippers into sCD40L proteins results in destabilization, the stability of these molecules can be improved by incorporating into their design short trimerization motifs such as those described by Morris et al. (62). Alternatively, the same goal can be achieved by incorporating into these chimeras the stalk domain of the CD40L protein in view of the recent finding by Su et al. (52) that showed the stalk domain of CD40 contributes to the stability of the CD40 trimer.

For functional validation of the zipper-tagged ligands, two key features of the newly derived zipper-sCD40L and zipper-anti-CD40 scFv proteins can be tested. Firstly, gel-filtration chromatography on Sephacryl S-200 HR can be used to prove that these proteins are trimeric. Secondly, the ability of the zipper-tagged sCD40L or anti-CD40 scFv proteins to bind CD40 can be addressed by FACS analysis using a CD40-expressing derivative of 293 cells, i.e. 293/CD40 generated in Dr. Krasnykh's laboratory at the Gene Therapy Center at University of Alabama. Parental 293 cells, which are CD40-negative, can be used as a negative control. This assay has been successfully used previously to demonstrate the binding specificity of 6His-tagged sCD40L proteins (FIG. 5B).

In order to show that the zipper-tagged ligands can form complexes with the relevant zipper-containing adenoviral vectors, protein chimeras purified by immobilized metal ion affinity chromatography can be mixed at various stochiometric ratios with CsCl-purified adenoviral virions containing the complementary zipper peptides and allowed to associate. Control mixtures contain the same amounts of the ligand protein and adenoviral vectors containing unmodified fibers. The mixtures are resolved by gel filtration on Sephacryl S-200 HR that allows separation of adenoviral virions (unconjugated and those linked with zipper-ligands) from unincorporated protein ligands. By collecting the fraction corresponding to free zipper-ligand proteins and measuring the volume of the sample and the protein concentration, the amounts of unincorporated/incorporated ligands can be calculated. Knowing the number of adenoviral particles incubated with the ligand and the amount of total ligand incorporated into the complex, average number of ligands associated with an adenoviral virion can be calculated. This will allow optimization of the vector-to-ligand ratio and provide an estimate of the efficiency of their association.

The ultimate test of the functional utility of the targeting complexes disclosed herein is their ability to deliver a transgene to CD40-positive cells. This can be done by infecting 293 and 293/CD40 cells with either the adenoviral vectors alone or with the adenoviral vectors linked with a ligand. As 293 cells express high levels of the native adenoviral receptor, the cells are preincubated with recombinant Ad5 fiber knob protein in order to block CAR-mediated gene delivery (45, 46, 59). When used at a final concentration of 50 µg/ml, the knob normally blocks Ad5 binding to CAR by 100-fold. Additionally, the receptor specificity of the targeting complexes can be confirmed by using recombinant sCD40L or G28.5 scFv as competitors of binding to CD40. Recombinant sCD40L or G28.5 scFv have been shown to compete with each other for binding to CD40 (37). Dose-dependent inhibition of CD40-mediated gene transfer can be obtained by varying the concentration of relevant competitor (fiber knob, sCD40L or G28.5 scFv). The levels of the virus-encoded luciferase activity detected in the lysates of infected cells 24 hrs post infection are used as a measure of transduction efficiency.

EXAMPLE 4

Derivation of Zipper-Ligand Encoding, Fiber-Modified Adenoviral Vector

One object of the present invention is to develop a targeted adenoviral vector as a single-component reagent capable of self-assembly of two elements, namely the adenoviral virion and the targeting ligand. This example describes the generation of zipper-modified adenoviral vector encoding a zipper-tagged ligand and examining its ability to self-assembly and target CD40-positive cells.

To construct a zipper-ligand encoding, fiber-modified adenoviral vector, a recombinant gene encoding the optimal configurations of a zipper-tagged targeting ligand as disclosed in Example 3 is modified to incorporate the human growth hormone secretory signal sequence and then cloned into the AdApt shuttle vector (Crucell, the Netherlands) designed for the generation of E1-deleted adenoviral genomes. The resultant plasmid is used for recombination with adenoviral genomes containing the gene for the relevant fiber-zipper protein. Subsequently, the newly made adenoviral genome is used to rescue the vector of interest. These procedures, as well as the molecular characterization of the resultant vector, can be done according to the methods described in Example 2.

To validate the expression and secretion of the newly constructed adenoviral vector, the ligand-encoding adenoviral vector is used to infect 293 cells. The time course of ligand secretion and its dependence on the MOI are established by infecting the cells at MOIs ranging from 0.1 to 100 focus-forming units. Small aliquots of the culture medium is collected at various time points post-infection until complete cell lysis is seen, at which point the rest of the medium together with the lysed cells are collected. The amount of the ligand in the samples can be estimated by Western blot using an anti-6His mAb. Furthermore, the last collected aliquots can be concentrated by ultrafiltration and adenoviral virions can be purified from it by ultracentrifugation in CsCl gradients. The protein composition of the purified vector can then be analyzed by western blot with anti-fiber and anti-ligand antibodies. These studies will identify the MOI which results in most efficient accumulation of ligand in the medium and optimal incorporation of the ligand into the targeting complex. Additionally, the ligand purified from the growth medium by immobilized metal ion affinity chromatography can be used for FACS analysis on 293/CD40 cells as described in Example 3 to examine its ability to bind the target receptor.

To evaluate the targeting properties of the ligand-adenoviral complex, the ability of the targeted vector to achieve CD40-mediated gene delivery to target cells can be examined according to the experimental design described in Example 3. As the newly made virus will no longer express a reporter gene, the gene transfer efficiency is quantitated by counting viral plaques visualized according to the method of Bewig (56).

EXAMPLE 5

Fos and Jun interact with each other to form the transcription factor AP-1. They interact with each other through a leucine zipper domain. This leucine zipper has been used in several other settings as well to fuse two different proteins to each other.

The Fos or Jun leucine zipper are incorporated into the pIX protein of the virus capsid. This allows the binding of Fos or Jun leucine zipper labeled proteins/targeting ligands onto the capsid.

The virus containing the Jun leucine zipper in the viral capsid has been rescued. The presence of the FLAG tag that is incorporated along with the leucine zipper has been demonstrated with Western Blot: the FLAG staining colocalizes with pIX staining, of about the right size. The virus containing the Fos leucine zipper in the capsid is constructed.

Fusion proteins containing either the Fos or Jun leucine zipper, fused to GFP and a scFv domain have been described. These reagents are bound to this virus to demonstrate the functionality of the leucine zipper on the pIX protein and to illustrate that one can incorporate targeting ligands such as scFv's and imaging molecules such as GFP to the virus.

The following references were cited herein:
1. Gong et al., Proc Natl Acad Sci U S A 95:6279–83 (1998).
2. Song et al., J Exp Med 186:1247–56 (1997).
3. Specht et al., J Exp Med 186:1213–21 (1997).
4. Zitvogel et al., J Exp Med 183:87–97 (1996).
5. Hsu et al., Nat Med 2:52–8 (1996).
6. Kugler et al., Nat Med 6:332–6 (2000).
7. Nestle et al., Nat Med 4:328–32 (1998).
8. Boon et al., Annu Rev Immunol 12:337–65 (1994).
9. Correale et al., J Natl Cancer Inst 89:293–300 (1997).
10. Coulie et al., Biochem Soc Trans 25:544–8 (1997).
11. Kwak et al., N Engl J Med 327:1209–15 (1992).
12. Pardoll, Immunol Today 14:310–6 (1993).
13. Robbins and Kawakami, Curr Opin Immunol 8:628–36 (1996).
14. Tjoa et al., Prostate 28:65–9 (1996).
15. Tsang et al., J Natl Cancer Inst 87:982–90 (1995).
16. Timmerman and Levy, Annu Rev Med 50:507–29 (1999).

17. Bocchia et al., Haematologica 85:1172–206 (2000).
18. Mayordomo et al., Stem Cells 15:94–103 (1997).
19. Fong and Engleman, Annu Rev Immunol 18:245–73 (2000).
20. Murphy et al., Prostate 39:54–9 (1999).
21. Brossart et al., J Immunol 158:3270–6 (1997).
22. Dietz and Vuk-Pavlovic, Blood 91:392–8 (1998).
23. Kaplan et al., J Immunol 163:699–707 (1999).
24. Rea et al., J Virol 73:10245–53 (1999).
25. Brand et al., Cancer Gene Ther 4:9–16 (1997).
26. Lozier et al., Blood 94:3968–75 (1999).
27. O'Neal et al., Hum Gene Ther 9:1587–98 (1998).
28. O'Neal et al., Mol Med 6:179–95 (2000).
29. Yee et al., Hum Gene Ther 7:1251–7 (1996).
30. Freimuth, J Virol 70:4081–5 (1996).
31. Asada-Mikami, et al., Jpn J Cancer Res 92:321–7 (2001).
32. Okada, et al., Biochem Biophys Res Commun 282:173–9 (2001).
33. Tillman et al., J Immunol 162:6378–83 (1999).
34. Banchereau and Steinman, Nature 392:245–52 (1998).
35. Lee et al., Transplantation 66:1810–7 (1998).
36. Pereboev, unpublished data.
37. Krasnykh and Belousova, unpublished data.
38. Hurst, Protein Profile 2:101–68 (1995).
39. Hodges, Biochem Cell Biol 74:133–54 (1996).
40. Moll et al., Protein Sci 10:649–55 (2001).
41. Arndt, et al., J Mol Biol 295:627–39 (2000).
42. Mathias et al., J Virol 72:8669–75 (1998).
43. Katz et al., Biotechniques 25:298–302, 304 (1998).
44. Pereboev et al., J Virol 75:7107–13 (2001).
45. Dmitriev et al., J Virol 72:9706–13 (1998).
46. Krasnykh et al., J Virol 72:1844–52 (1998).
47. Michael et al., Gene Ther 2:660–8 (1995).
48. Wickham et al., Nat Biotechnol 14:1570–3 (1996).
49. Wickham et al., J Virol 71:8221–9 (1997).
50. Belousova et al., Molecular Therapy 3:S168 (2001).
51. Parrot and Barry, Molecular Therapy 3:S165 (2001).
52. Su et al., J Biol Chem 276:1673–6 (2001).
53. Hong and Engler, J Virol 70:7071–8 (1996).
54. Dmitriev et al., J Virol 74:6875–84 (2000).
55. Mittereder et al., J Virol 70:7498–509 (1996).
56. Bewig and Schmidt, Biotechniques 28:870–3 (2000).
57. Pullen, et al., Biochemistry 38:10168–77 (1999).
58. Zeng, Biotechniques 25:206–8 (1998).
59. Krasnykh et al., J Virol 70:6839–46 (1996).
60. Krasnykh et al., J Virol 75:4176–83 (2001).
61. Von Seggern et al., J Gen Virol 79:1461–8 (1998).
62. Morris et al., J Biol Chem 274:418–23 (1999).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A targeted recombinant adenovirus vector, comprising:
   (i) a gene encoding a heterologous protein;
   (ii) a modified fiber protein comprising a first zipper peptide, wherein said first zipper peptide is capable of forming heteroduplex with a second zipper peptide via formation of coiled coils; and
   (iii) a gene encoding a fusion protein comprising said second zipper peptide and a targeting ligand, wherein binding of said first zipper peptide to said second zipper peptide connects said targeting ligand to said modified fiber protein, thereby targeting said adenovirus vector to a cell that expresses a cell surface molecule that binds to said targeting ligand, wherein said zipper peptides are selected from the group consisting of SEQ ID NOs: 1, 2, 3, and 4.

2. A targeted recombinant adenovirus vector, comprising:
   (i) a gene encoding a heterologous protein;
   (ii) a modified fiber protein comprising a first zipper peptide, wherein said first zipper peptide is capable of forming heteroduplex with a second zipper peptide via formation of coiled coils; and
   (iii) a gene encoding a fusion protein comprising said second zipper peptide and a targeting ligand, wherein binding of said first zipper peptide to said second zipper peptide connects said targeting ligand to said modified fiber protein, thereby targeting said adenovirus vector to a cell that expresses a cell surface molecule that binds to said targeting ligand, wherein said first zipper peptide is inserted at an HI loop or the carboxy terminus of said fiber protein.

3. A targeted recombinant adenovirus vector, comprising:
   (i) a gene encoding a heterologous protein;
   (ii) a modified fiber protein comprising a first zipper peptide, wherein said first zipper peptide is capable of forming heteroduplex with a second zipper peptide via formation of coiled coils; and
   (iii) a gene encoding a fusion protein comprising said second zipper peptide and a targeting ligand, wherein binding of said first zipper peptide to said second zipper peptide connects said targeting ligand to said modified fiber protein, thereby targeting said adenovirus vector to a cell that expresses a cell surface molecule that binds to said targeting ligand, wherein said fiber protein is a fiber-fibritin chimera, and said first zipper peptide is inserted at the carboxy terminus of said fiber-fibritin chimera.

4. A CD40-targeted recombinant adenovirus vector, comprising:
   (i) a gene encoding a heterologous protein;
   (ii) a modified fiber protein comprising a first zipper peptide, wherein said first zipper peptide is capable of forming heteroduplex with a second zipper peptide via formation of coiled coils; and
   (iii) a gene encoding a fusion protein comprising said second zipper peptide and a targeting ligand selected from the group consisting of CD40 ligand and a single chain fragment (scFv) of anti-human CD40 antibody, wherein binding of said first zipper peptide to said second zipper peptide connects said targeting ligand to said modified fiber protein, thereby targeting said adenovirus vector to a CD40⁺ cell, wherein said zipper peptides are selected from the group consisting of SEQ ID NOs: 1, 2, 3, and 4.

5. CD4-targeted recombinant adenovirus vector, comprising:
(i) a gene encoding a heterologous protein;
(ii) a modified fiber protein comprising a first zipper peptide, wherein said first zipper peptide is capable of forming heteroduplex with a second zipper peptide via formation of coiled coils; and
(iii) a gene encoding a fusion protein comprising said second zipper peptide and a targeting ligand selected from the group consisting of CD40 ligand and a single chain fragment (scFv) of anti-human CD40 antibody, wherein binding of said first zipper peptide to said second zipper peptide connects said targeting ligand to said modified fiber protein, thereby targeting said adenovirus vector to a CD40⁺ cell, wherein said first zipper peptide is inserted at an HI loop or the carboxy terminus of said fiber protein.

6. CD40-targeted recombinant adenovirus vector, comprising:
(i) a gene encoding a heterologous protein;
(ii) a modified fiber protein comprising a first zipper peptide, wherein said first zipper peptide is capable of forming heteroduplex with a second zipper peptide via formation of coiled coils; and
(iii) a gene encoding a fusion protein comprising said second zipper peptide and a targeting ligand selected from the group consisting of CD40 ligand and a single chain fragment (scFv) of anti-human CD40 antibody, wherein binding of said first zipper peptide to said second zipper peptide connects said targeting ligand to said modified fiber protein, thereby targeting said adenovirus vector to a CD40⁺ cell, wherein said fiber protein is a fiber-fibritin chimera, and said first zipper peptide is inserted at the carboxy terminus of said fiber-fibritin chimera.

* * * * *